US007045451B2

(12) United States Patent
Shenai-Khatkhate

(10) Patent No.: US 7,045,451 B2
(45) Date of Patent: May 16, 2006

(54) PREPARATION OF GROUP IVA AND GROUP VIA COMPOUNDS

(75) Inventor: Deodatta Vinayak Shenai-Khatkhate, Danvers, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 242 days.

(21) Appl. No.: 10/817,571

(22) Filed: Apr. 2, 2004

(65) Prior Publication Data

US 2004/0198042 A1    Oct. 7, 2004

Related U.S. Application Data

(60) Provisional application No. 60/513,471, filed on Oct. 22, 2003, provisional application No. 60/513,476, filed on Oct. 22, 2003, provisional application No. 60/460,791, filed on Apr. 5, 2003.

(51) Int. Cl.
    *H01L 21/28*      (2006.01)
    *H01L 21/3205*   (2006.01)

(52) U.S. Cl. ...................... 438/602; 438/603; 438/604; 438/513; 438/680

(58) Field of Classification Search ................ 438/602, 438/603, 604, 513, 608, 676, 677, 678, 679, 438/681, 255, 480, 752, 753, 503, 507, 933
See application file for complete search history.

(56) References Cited

U.S. PATENT DOCUMENTS

| | | | |
|---|---|---|---|
| 2,444,270 | A | 6/1948 | Rochow |
| 3,446,824 | A | 5/1969 | Moedritzer |
| 3,470,220 | A | 9/1969 | Moedritzer et al. |
| 3,935,040 | A | 1/1976 | Mason |
| 3,985,590 | A | 10/1976 | Mason |
| 4,506,815 | A | 3/1985 | Melas et al. |
| 4,720,561 | A | 1/1988 | Bradley et al. |
| 4,812,586 | A | 3/1989 | Mullin et al. |
| 5,120,394 | A | 6/1992 | Mukai |
| 5,316,958 | A | 5/1994 | Meyerson |
| 5,442,112 | A * | 8/1995 | Cole-Hamilton et al. ... 562/899 |
| 5,489,550 | A | 2/1996 | Moslehi |
| 5,502,227 | A | 3/1996 | Kanjolia et al. |
| 5,755,885 | A | 5/1998 | Mikoshiba et al. |
| 6,067,785 | A * | 5/2000 | Russell et al. ............. 57/400 |
| 6,099,903 | A | 8/2000 | Kaloyeros et al. |
| 6,214,729 | B1 | 4/2001 | Uhlenbrock et al. |
| 6,238,734 | B1 | 5/2001 | Senzaki et al. |
| 6,306,217 | B1 | 10/2001 | Uhlenbrock et al. |
| 6,391,803 | B1 | 5/2002 | Kim et al. |
| 6,444,038 | B1 | 9/2002 | Rangarajan et al. |
| 6,444,041 | B1 * | 9/2002 | Vaartstra .................... 118/715 |
| 6,444,818 | B1 | 9/2002 | Uhlenbrock et al. |
| 6,492,711 | B1 | 12/2002 | Takagi et al. |
| 6,509,587 | B1 | 1/2003 | Sugiyama et al. |
| 6,514,886 | B1 | 2/2003 | U'Ren |
| 2003/0082300 | A1 | 5/2003 | Todd et al. |
| 2003/0111013 | A1 | 6/2003 | Oosterlaken et al. |
| 2003/0230233 | A1 | 12/2003 | Fitzgerald et al. |
| 2004/0259333 | A1 | 12/2004 | Tomasini et al. |

FOREIGN PATENT DOCUMENTS

| | | |
|---|---|---|
| EP | 0 368 651 B1 | 9/1994 |
| EP | 1 160 355 A2 | 12/2001 |
| GB | 626398 | 4/1946 |
| GB | 1 386 900 | 3/1975 |
| WO | WO 2004/011473 A1 | 2/2004 |

OTHER PUBLICATIONS

Masaki Okamoto; Direct Syntehsis of Organotrichlorogermanes by the Reaction of Elemental Germanium, Hydrogen Chloride and Alkene; Organometallics 2004, 23, pp. 595-599.

Bradley et al.; "Synthesis and characterisation of trialkylaluminium-dialkytamine adducts: X-ray diffraction and $^1$H NMR studies"; J. Chem. Soc., Dalton Trans. 1999, pp. 3553-3558.

Dittmar et al., Cyclopentadienyl Germanes as Novel Precursors for the CVD of Thin Germanium Films, Chem. Vap. Deposition 2001, 7, No. 5, pp. 193-195.

Harrison et al., "Predeposition Chemistry Underlying the Formation of Germanium Films by CVD of Tetravinylgermane", Chem. Mater. 1994, 6, pp. 1620-1626.

Hoffman et al., "Plasma-enhanced chemical vapor deposition of silicon, germanium, and tin nitride thin films from metalorganic precursors", J. Vac. Sci. Technol. A 13(3), May/Jun. 1995, pp. 820-825.

O. Johnson, "The Germanes and Their Organo Derivatives", Chem. Rev. 1951, 48, 259, pp. 259-297.

Kidd et al., "Germanium-73 Nuclear Magnetic Resonance Spectra of Germanium Tetrahalides", Journal of American Chemical Society, 95:1, Jan. 10, 1973, pp. 88-90.

H. Ohshima, "Organo-germanium adsorption on a silicon surface by excimer light irradiation", Applied Surface Science 107 (1996) pp. 85-89.

Bottei et al., "Organogermanium Chemistry", Chem. Rev. (1951), 48, 259, pp. 403-442.

Sulkes et al., "Molecular beam study of possible CVD intermediates from Group-14 organometallic precursors", Chemical Physics Letters 318 (2000) pp. 448-453.

D. Smith, Structural Properites of heteroepitaxial germanium-carbon alloys grown on Si (100); Philosophical Magazine A, 2001, vol. 81, No. 6, pp. 1613-1624.

Todd et al., "Influence on Precursor Chemistry on Synthesis of Silicon-Carbon Germanium Alloys", Mat. Res. Soc. Symp. Proc. vol. 377, 1955, pp. 529-534.

(Continued)

*Primary Examiner*—David Nhu
(74) *Attorney, Agent, or Firm*—S. Matthew Cairns

(57) ABSTRACT

Methods of preparing Group IVA and Group VIA organometallic compounds, particularly Group IVA organometallic compounds, are provided. Such manufacturing methods employ an amine and/or phosphine catalyst in a transalkylation step and may be performed in a batch, semi-continuous or continuous manner.

10 Claims, No Drawings

OTHER PUBLICATIONS

Dillon et al.; "Comparison of Trichlorosilane and Trichlorogermane Decomposition on Silicon Surfaces Using FTIR Spectroscopy"; Mat. Res. Soc. Symp. Proc. vol. 282; 1993; pp. 405-411.

Dillon et al.; "Adsorption and Decomposition of Diethylgermane on porous silicon surfaces"; Surface Science Letters 286 (1993); pp. L535-L541.

Todd et al.; Chemical Synthesis of Metastable Germanium-Carbon Alloys Grown Heteroepitaxially on (100) Si; Chem. Mater. 1996, 8, pp. 2491-2498.

Coon et al.; "Germanium Deposition on Silicon: Surface Chemistry of $(CH_3CH_2)_2GeH_2$ and $GeCl_4$"; Mat. Res. Soc. Symp. Proc. vol. 282; 1993; pp. 413-419.

Kouvetakis et al.; "Novel Chemical Routes to Silicon-Germanium-Carbon Materials"; Appl. Phys. Lett. 65 (23); Dec. 5, 1994; pp. 2960-2962.

Dillon et al.; "Adsorption and Decomposition of Trichlorosilane and Trichlorogermane on Porous Silicon and Si(100)2×1 Surfaces"; J. Vac. Sci. Technol. A 13(1); Jan./Feb. 1995; pp. 1-10.

* cited by examiner

PREPARATION OF GROUP IVA AND GROUP VIA COMPOUNDS

This application claims benefit of Ser. No. 60/460,791 filed Apr. 5, 2003 and claims benefit of Ser. No. 60/513,471 filed Oct. 22, 2003 and claims benefit of Ser. No. 60/513,476 filed Oct. 22, 2003.

BACKGROUND OF THE INVENTION

The present invention relates to the field of Group IV compounds. In particular, this invention relates to the preparation of Group IV organometallic compounds suitable for use in chemical vapor deposition.

Metal films may be deposited on surfaces, such as non-conductive surfaces, by a variety of means such as chemical vapor deposition ("CVD"), physical vapor deposition ("PVD"), and other epitaxial techniques such as liquid phase epitaxy ("LPE"), molecular beam epitaxy ("MBE"), chemical beam epitaxy ("CBE") and atomic layer deposition ("ALD"). Chemical vapor deposition processes, such as metalorganic chemical vapor deposition ("MOCVD"), deposit a metal layer by decomposing organometallic precursor compounds at elevated temperatures, i.e., above room temperature, either atmospheric pressure or at reduced pressures. A wide variety of metals may be deposited using such CVD or MOCVD processes.

For semiconductor and electronic device applications, these organometallic precursor compounds must be highly pure and be substantially free of detectable levels of both metallic impurities, such as silicon and zinc, as well as oxygenated impurities. Oxygenated impurities are typically present from the solvents used to prepare such organometallic compounds, and are also present from other adventitious sources of moisture or oxygen.

For certain applications where high speed and frequency response of an electronic device is desired, silicon-only devices, e.g. silicon bipolar transistors, have not been competitive. In a heterojunction bipolar transistor ("HBT"), a thin silicon-germanium layer is grown as the base of a bipolar transistor on a silicon wafer. The silicon-germanium HBT has significant advantages in speed, frequency response, and gain when compared to a conventional silicon bipolar transistor. The speed and frequency response of a silicon-germanium HBT are comparable to more expensive gallium-arsenide HBTs.

The higher gain, speeds, and frequency response of silicon-germanium HBTs have been achieved as a result of certain advantages of silicon-germanium not available with pure silicon, for example, narrower band gap and reduced resistivity. Silicon-germanium may be epitaxially grown on a silicon substrate using conventional silicon processing and tools. This technique allows one to engineer device properties such as the energy band structure and carrier mobility. For example, it is known in the art that grading the concentration of germanium in the silicon-germanium base builds into the HBT device an electric field or potential gradient, which accelerates the carriers across the base, thereby increasing the speed of the HBT device compared to a silicon-only device. A common method for fabricating silicon and silicon-germanium devices is by CVD. A reduced pressure chemical vapor deposition technique ("RPCVD") used to fabricate the HBT device allows for a controlled grading of germanium concentration across the base layer as well as precise control over the doping profile.

Germane ($GeH_4$) is the conventional precursor for germanium deposition while silane ($SiH_4$), and dichlorosilane ($SiH_2Cl_2$) are conventional precursors for silicon deposition. These precursors are difficult to handle and have high vapor pressures. For example, germane decomposes violently at 280° C., which is below the temperature used to grow germanium films. Accordingly, processes employing either germane or silane require extensive safety procedures and equipment. Germane typically requires film growth temperatures of approximately 500° C. or higher for thermal CVD applications. Such decomposition temperatures are not always suitable, such as in mass production applications where there is a need for lower temperatures, e.g. 200° C. Other CVD applications require higher growth temperatures, which cause conventional precursors to break up prematurely which, in turn, leads to the formation of particles and a reduction in metal film growth rates. A further problem with conventional silicon and germanium precursors is that when a relatively stable silicon precursor and a relatively unstable germanium precursor are used to deposit a silicon-germanium film, the differences in precursor stability make control of the silicon-germanium composition difficult.

There is a need for precursors for silicon and germanium vapor phase deposition that are safer to handle and have decomposition temperatures that are tailored to specific conditions. Certain silicon and germanium precursors having desirable properties for use as CVD precursors include the organosilicon hydrides, organogermanium hydrides and heteroleptic organosilicon and organogermanium compounds. Such Group IV organometal precursors may be difficult to prepare and may involve multiple steps. For example, the use of trialkylaluminum compounds for the alkylation of Group IVA metals (e.g., silicon, germanium and tin) and Group VIA metals (e.g., selenium and tellurium) has not been successful because of certain problems encountered. For example, the reactions between aluminum alkyls and germanium halides are known to produce di- and poly-germanes rather than desired alkylgermanes as final products. Similarly, the reaction between tellurium halides and organoaluminums is known to form aluminum telluride as the final product rather than the desired dialkyltellurides.

Accordingly, the reactions employed for the synthesis of Group IVA and Group VIA organometallics are primarily based on organolithium and organomagnesium compounds. These reactions inherently involve the use of ethereal solvents that are extremely difficult to remove at ppm levels. Also, organotellurides are known to be commercially synthesized in high yields by using aqueous medium and in the presence of a phase transfer catalyst. See, for example, U.S. Pat. No. 5,442,112. Such processes involve oxygenated solvents and thus create serious quality concerns for the use of these products in certain electronics applications, where trace oxygen and organics are known to catastrophically affect the optoelectronic properties of the fabricated devices.

Accordingly, there is a need for a method of preparing organometallic compounds, such as Group IVA and Group VIA alkylmetal compounds, for use as CVD precursors where such method involves fewer steps than conventional methods, and where such compounds are substantially oxygen-free.

SUMMARY OF THE INVENTION

It has been found that certain organometallic compounds, particularly Group IVA and Group VIA alkylmetal compounds, can be prepared in high yield and in high purity using certain organometal exchange reactions and a tertiary amine and/or tertiary phosphine. The tertiary amine and/or tertiary phosphine is typically used in catalytic amounts. Organometallic compounds produced by this method are extremely pure and substantially free of oxygenated impurities.

The present invention provides a method of preparing an organometallic compound comprising the step of reacting a metal halide of the formula $R_mMX_{4-m}$ with a Group IIIA compound of the formula $R^1{}_nM^1X^1{}_{3-n}$ in the presence of a catalyst chosen from a tertiary amine, a tertiary phosphine and mixtures thereof in an organic solvent to provide an alkylmetal compound, wherein each R is independently chosen from H, alkyl, alkenyl, alkynyl and aryl; M is chosen from a Group IVA metal and a Group VIA metal; each X is independently a halogen; each $R^1$ is independently chosen from $(C_1-C_6)$alkyl; $M^1$ is a Group IIIA metal; each $X^1$ is independently a halogen; m=0–3; and n=1–3. Such reaction may be performed in a variety of ways such as batch, semi-continuous and continuous. The organometallic compounds produced by this method may be used as precursor compounds for chemical vapor deposition of metal-containing films or may be further reacted to form other organometallic compounds.

The present invention further provides a method for depositing a metal-containing film, where the metal is chosen from one or more of a Group IVA metal and a Group VIA metal, on a substrate including the steps of: a) conveying one or more source compounds chosen from a Group IVA metal source compound and a Group VIA metal source compound in the gaseous phase to a deposition chamber containing the substrate; b) decomposing the one or more source compounds in the deposition chamber; and c) depositing the metal-containing film on the substrate; wherein one or more of the Group IVA metal source compounds and Group VIA metal source compounds is prepared by the method including the step of reacting a metal halide of the formula $R_mMX_{4-m}$ with a Group IIIA compound of the formula $R^1{}_nM^1X^1{}_{3-n}$ in the presence of a catalyst chosen from a tertiary amine, a tertiary phosphine and mixtures thereof in an organic solvent, wherein each R is independently chosen from H, alkyl, alkenyl, alkynyl and aryl; M is chosen from a Group IVA metal and a Group VIA metal; each X is independently a halogen; each $R^1$ is independently chosen from $(C_1-C_6)$alkyl; $M^1$ is a Group IIIA metal; each $X^1$ is independently a halogen; m=0–3; and n=1–3.

Also provided are Group IVA and Group VIA organometallic compounds made by the method described above.

DETAILED DESCRIPTION OF THE INVENTION

As used throughout this specification, the following abbreviations shall have the following meanings, unless the context clearly indicates otherwise: ° C.=degrees centigrade; mol=moles; b.p.=boiling point; g=gram; L=liter; µm=micron=micrometer; cm=centimeter; ppm=parts per million; and mL=milliliter.

"Halogen" refers to fluorine, chlorine, bromine and iodine and "halo" refers to fluoro, chloro, bromo and iodo. Likewise, "halogenated" refers to fluorinated, chlorinated, brominated and iodinated. "Alkyl" includes linear, branched and cyclic alkyl. Likewise, "alkenyl" and "alkynyl" include linear, branched and cyclic alkenyl and alkynyl, respectively. The term "SiGe" refers to silicon-germanium. The term "Group IVA metal" is not intended to include Group IV non-metals such as carbon. Likewise, the term "Group VIA metal" is not intended to include Group VI non-metals such as oxygen and sulfur. "Aryl" refers to any aromatic moiety, and preferably an aromatic hydrocarbon.

The articles "a" and "an" refer to the singular and the plural. As used herein, "CVD" is intended to include all forms of chemical vapor deposition such as MOCVD, MOVPE, OMVPE, OMCVD and RPCVD.

Unless otherwise noted, all amounts are percent by weight and all ratios are molar ratios. All numerical ranges are inclusive and combinable in any order except where it is clear that such numerical ranges are constrained to add up to 100%.

The present invention provides a method of preparing organometallic compounds of Group IVA and Group VIA metals, including a transalkylation step. Such organometallic compounds are particularly suitable for use as precursors (or source compounds) in CVD processes. Such organometallic compounds are prepared by a process including the step of: reacting a metal halide of the formula $R_mMX_{4-m}$ with a Group IIIA compound of the formula $R^1{}_nM^1X^1{}_{3-n}$ in the presence of a tertiary amine or a tertiary phosphine or mixtures of a tertiary amine and a tertiary phosphine in an organic solvent to provide an alkylmetal compound, wherein each R is independently chosen from H, alkyl, alkenyl, alkynyl and aryl; M is chosen from a Group IVA metal and a Group VIA metal; each X is independently a halogen; each $R^1$ is independently chosen from $(C_1-C_6)$alkyl; $M^1$ is a Group IIIA metal; each $X^1$ is independently a halogen; m=0–3; and n=1–3. The Group IVA metal halides and the Group VIA metal halides are generally commercially available, such as from Gelest, Inc. (Tullytown, Pa.), or may be prepared by methods known in the literature. Such compounds may be used as is or may be purified prior to use. It will be appreciated by those skilled in the art that more than one metal halide, more than one Group IIIA compound, and combinations thereof may be used.

Exemplary Group IVA metals include, but are not limited to, silicon, germanium and tin. Exemplary Group VIA metals include, without limitation, tellurium and selenium. M is preferably silicon, germanium or tin and more preferably germanium. X may be any halogen. Each X may be the same or different. In one embodiment, m=0. When m=0, a Group IVA or Group VIA metal tetrahalide is used. In other embodiments, m may be 1, 2 or 3.

A wide variety of alkyl, alkenyl and alkynyl groups may be used for R. Suitable alkyl groups include, without limitation, $(C_1-C_{12})$alkyl, typically $(C_1-C_6)$alkyl and more typically $(C_1-C_4)$alkyl. In one embodiment, the alkyl groups are bulky alkyl groups. By "bulky alkyl group" is meant any sterically hindered alkyl group. Such bulky alkyl groups have at least three carbons, there being no particular upper limit to the number of carbons in such group. It is preferred that the bulky alkyl groups each have from three to six carbon atoms, and more preferably three to five carbon atoms. Such bulky alkyl groups are preferably not linear, and are preferably cyclic or branched. Exemplary alkyl groups include methyl, ethyl, n-propyl, iso-propyl, n-butyl, iso-butyl, sec-butyl, tert-butyl, pentyl, cyclopentyl, hexyl, and cyclohexyl. More typically, suitable alkyl groups include ethyl, iso-propyl, and tert-butyl. Suitable alkenyl groups include, without limitation, $(C_2-C_{12})$alkenyl, typically $(C_2-C_6)$alkenyl and more typically $(C_2-C_4)$alkenyl. Exemplary alkenyl groups include vinyl, allyl, methallyl and crotyl. Typical alkynyl groups include, without limitation, $(C_2-C_{12})$alkynyl, typically $(C_2-C_6)$alkynyl and more typically $(C_2-C_4)$alkynyl. Suitable aryl groups are $(C_6-C_{10})$aryl, including, but not limited to, phenyl, tolyl, xylyl, benzyl and phenethyl. When two or more alkyl, alkenyl or alkynyl groups are present, such groups may be the same or different.

Any of the above alkyl, alkenyl, alkynyl or aryl groups of R may optionally be substituted, such as with halogen or dialkylamino. By "substituted" it is meant that one or more hydrogens on the alkyl, alkenyl, alkynyl or aryl group are replaced with one or more halogens or dialkylamino groups.

A wide variety of Group IIIA compounds may be used in the present invention. Suitable Group IIIA compounds useful in the present invention typically have the formula $R^1{}_nM^1X^1{}_{3-n}$, wherein each $R^1$ is independently selected from $(C_1-C_6)$alkyl; $M^1$ is a Group IIIA metal; $X^1$ is halogen; and n is an integer from 1 to 3. $M^1$ is suitably boron, aluminum, gallium, indium and thallium, and preferably aluminum. Preferably, $X^1$ is selected from fluorine, chlorine or bromine. Suitable alkyl groups for $R^1$ include, but are not limited to, methyl, ethyl, n-propyl, iso-propyl, n-butyl, iso-butyl, and tert-butyl. Preferred alkyls include, methyl, ethyl, n-propyl and iso-propyl. In one embodiment, n is 3. Such Group IIIA compounds where n is 3 include trialkylboron, trialkylaluminum, trialkylgallium, trialkylindium and trialkylthallium, with trialkylaluminum compounds being preferred. In an alternate embodiment, n is 1 or 2. Such Group IIIA compounds where n is 1–2 include dialkylaluminum halides such as dialkylaluminum chlorides. Group IIIA compounds are generally available commercially from a variety of sources, such as Gelest, or may be prepared by a variety of methods known in the literature. Such compounds may be used as is or may be purified prior to use.

Any tertiary amine or tertiary phosphine may suitably be used in the present invention. Suitable tertiary amines include, but are not limited to, those having the general formula $NR^4R^5R^6$, wherein $R^4$, $R^5$ and $R^6$ are independently selected from $(C_1-C_6)$alkyl, di$(C_1-C_6)$alkylamino-substituted $(C_1-C_6)$alkyl, and phenyl and wherein $R^4$ and $R^5$ may be taken together along with the nitrogen to which they are attached to form a 5–7 membered heterocyclic ring. Such heterocyclic ring may be aromatic or non-aromatic. Particularly suitable tertiary amines include, but are not limited to, trimethylamine, triethylamine, tri-n-propylamine, tri-n-butylamine, tri-iso-propylamine, tri-iso-butylamine, dimethylaminocyclohexane, diethylaminocyclohexane, dimethylaminocyclopentane, diethylaminocyclopentane, N-methylpyrrolidine, N-ethylpyrrolidine, N-n-propylpyrrolidine, N-iso-propylpyrrolidine, N-methylpiperidine, N-ethylpiperidine, N-n-propylpiperidine, N-iso-propylpiperidine, N,N'-dimethylpiperazine, N,N'-diethylpiperazine, N,N'-dipropylpiperazine, N,N,N',N'-tetramethyl-1,2-diaminoethane, pyridine, pyrazine, pyrimidine, and mixtures thereof. Preferred amines include trimethylamine, triethylamine, tri-n-propylamine, triiso-propylamine, and tri-n-butylamine. In one embodiment, the tertiary amine is triethylamine or tri-n-propylamine.

Exemplary tertiary phosphines include, without limitation, those of the general formula $R^7R^8R^9P$, where $R^7$, $R^8$, and $R^9$ are independently chosen from $(C_1-C_6)$alkyl, phenyl and $(C_1-C_6)$alkyl-substituted phenyl. Suitable tertiary phosphines include triethyl phosphine, tripropyl phosphine, tributyl phosphine, phenyl dimethyl phosphine, phenyl diethyl phosphine and butyl diethyl phosphine.

It will be appreciated by those skilled in the art that more than one tertiary amine or tertiary phosphine may be used in the present invention. Mixtures of a tertiary amine and a tertiary phosphine may also be used. Such tertiary amines and tertiary phosphines are generally commercially available from a variety of sources. Such tertiary amines and tertiary phosphines may be used as is or, preferably further purified prior to use.

A wide variety of organic solvents may be used in the present invention. Typically, such organic solvents do not contain oxygenated species such as ether linkages, and are preferably free of oxygen. Exemplary organic solvents include, but are not limited to, hydrocarbons and aromatic hydrocarbons. Suitable organic solvents include, without limitation, benzene, toluene, xylene, pentane, hexane, heptane, octane, decane, dodecane, squalane, cyclopentane, cyclohexane, cycloheptane, and mixtures thereof. It will be appreciated that more than one organic solvent may be advantageously used in the present invention. In an alternative embodiment, the tertiary amine may be used as the organic solvent. Such organic solvents are generally commercially available from a variety of sources, such as Aldrich (Milwaukee, Wis.). Such solvents may be used as is or, preferably, purified prior to use.

Preferably, such organic solvents are deoxygenated prior to use. The solvents may be deoxygenated by a variety of means, such as purging with an inert gas, degassing the solvent in vacuo, or a combination thereof. Suitable inert gases include argon, nitrogen and helium, and preferably argon or nitrogen.

The specific tertiary amine, tertiary phosphine and organic solvent used depend upon the particular alkylmetal compound desired. For example, the organic solvent and tertiary amine may be selected such that they are more volatile or less volatile than the desired alkylmetal compound. Such differences in volatility provide easier separation of the alkylmetal compound from both the amine and organic solvent. The selection of the tertiary amine and the organic solvent are well within the abilities of those skilled in the art.

In general, the tertiary amine and/or tertiary phosphine is present in a stoichiometric amount to the Group IIIA compound. The mole ratio of the metal halide to the Group IIIA compound may vary over a wide range, such as from 1:0.1 to 1:5, the particular mole ratio being dependent upon the alkylmetal compound desired. Another suitable range of mole ratios is from 1:0.5 to 1:2. Mole ratios greater than 1:5 are also expected to be effective.

The particular alkylmetal compound obtained from the present method can be controlled by selection of the mole ratio of the metal halide and the Group IIIA compound, i.e. the number of halogens replaced in the metal halide compound can be controlled by the number of moles of Group IIIA compound. For example, in the reaction of a Group IVA metal tetrahalide (A), such as germanium tetrachloride, with a trialkylaluminum (B), such as trimethylaluminum, a mole ratio of 1:0.5 (A:B) provides an alkyl Group IVA metal trihalide; a mole ratio of 1:1 (A:B) provides a dialkyl Group IVA metal dihalide; a mole ratio of 1:1.5 (A:B) provides a trialkyl Group IVA metal halide; and a mole ratio of 1:2 (A:B) provides a tetraalkyl Group IVA metal. Thus, one, two, three or four halogens of the metal halide compound may be replaced according to the present method.

In one embodiment, the Group IIIA compound, tertiary amine and/or tertiary phosphine and organic solvent may be combined in any order prior to reaction with the metal halide. In a further embodiment, the Group IIIA compound is first combined with the tertiary amine and/or tertiary phosphine to form an amine-Group IIIA adduct or a phosphine-Group IIIA adduct. Typically, the amine-Group IIIA adduct may be formed at a wide variety of temperatures.

Suitable temperatures for forming the adduct are from ambient to 90° C. The metal halide is then reacted with the amine-Group IIIA adduct to form the desired alkylmetal compound. It is preferred that the metal halide is added dropwise, either neat or as a hydrocarbon solution, to the amine-Group IIIA adduct. Alternatively, the amine-Group IIIA adduct may be added dropwise to the metal halide, either neat or as a hydrocarbon solution. Suitable temperatures to form the alkylmetal compound are from ambient to 80° C. Thus, in one embodiment, the present invention provides a method for preparing alkylmetal compounds including the steps of reacting a Group IIIA compound with a tertiary amine to form an amine-Group IIIA adduct in an organic solvent that is free of oxygenated species; and reacting the amine-Group IIIA adduct with a Group IVA metal halide, Group VIA metal halide or a mixture thereof in the organic solvent. When a tertiary phosphine is used in the above reactions, a phosphine-Group IIIA adduct is formed.

In another embodiment, the metal halide may be combined with the Group IIIA compound and optionally an organic solvent prior to the addition of the tertiary amine and/or tertiary phosphine. The tertiary amine and/or tertiary phosphine and optionally an organic solvent may then be added, such as by dropwise addition, to the metal halide-Group IIIA compound mixture. Alternatively, the metal halide-Group IIIA compound may be added, such as by dropwise addition, to the tertiary amine and/or tertiary phosphine and optionally an organic solvent. While not intending to be bound by theory, it is believed that the transalkylation reaction does not begin until the metal halide, Group IIIA compound and tertiary amine are combined.

Alternatively, the alkylmetal compound may be prepared in a continuous manner. For example, the metal halide and the Group IIIA compound may be independently added in a continuous manner to a reaction vessel containing tertiary amine and/or tertiary phosphine in a suitable solvent, such as an aromatic or aliphatic hydrocarbon having a b.p. of $\geq 150°$ C. The addition of the metal halide and the Group IIIA compound can be controlled by a variety of suitable means, such as by the use of mass flow controllers. In such a continuous process, the desired alkylmetal compound may be removed, such as by distillation, while the metal halide and Group IIIA compound are being added to the reaction vessel. In a further alternative, a mixture of the metal halide and the Group IIIA compound may be added to the tertiary amine and/or tertiary phosphine in a suitable solvent. In such a continuous process, the desired alkylmetal compound may be removed, such as by distillation, while the metal halide/Group IIIA compound mixture is being added to the reaction vessel. Such continuous operation requires periodic or continuous replenishment of the tertiary amine.

The alkylmetal compounds of the present invention may be used as is or suitably purified by a variety of techniques, such as by distillation, sublimation, and recrystallization. The present method provides alkylmetal compounds that are substantially free of metallic impurities such as aluminum, gallium, indium, cadmium, mercury and zinc. The alkylmetal compounds are also substantially free of oxygenated impurities such as ethereal solvents, and preferably free of such oxygenated impurities. By "substantially free" it is meant that the present compounds contain less than 0.5 ppm of such impurities. Typically, the present alkylmetal compounds have a purity of "6-nines", i.e. they are 99.9999% pure.

Alkylmetal compounds produced by the present method are suitable for use as metal precursors in CVD processes. When the alkylmetal compound includes one or more halogens, such alkylmetal compound may be further reacted to replace the one or more halogens. In one embodiment, an alkylmetal compound containing one or more halogens may be reacted with a second Group IIIA compound in the presence of a tertiary amine and/or tertiary phosphine to produce an alkylmetal compound containing at least two different alkyl groups. For example, germanium tetrabromide may be reacted with trimethylaluminum in a mole ratio of 1:0.5 according to the present method to provide methyl germanium tribromide. The methyl germanium tribromide may then be reacted with triethylaluminum in a mole ratio of 1:1 according to the present method to provide methyl diethyl germanium bromide. Such methyl diethyl germanium bromide may be used as is, or may be further reacted with a third Group IIIA compound if desired, or may be further reacted as described below.

In another embodiment, alkylmetal compounds including one or more halogens may be reacted with a reducing agent, i.e. reduced, to provide alkylmetal hydride compounds. A wide variety of reducing agents may be used in the present invention. Particularly useful reducing agents include, without limitation, borohydride reducing agents such as sodium borohydride and lithium borohydride; aluminum hydride reducing agents such as lithium aluminum hydride and $NaAlH_2(OCH_2CH_2OCH_3)_2$; borane reducing agents such as dimethylamine borane, cyclohexylamine borane, morpholine borane and alane reducing agents such as trimethylamine alane, methyl pyrrolidine alane, and dimethyl ethylamine alane. Aluminum hydride reducing agents are preferred.

In general, Group IVA and Group VIA alkylmetal hydride compounds are prepared by reacting the alkylmetal halide compound with a reducing agent in an organic solvent and in the presence of a tertiary amine and/or tertiary phosphine. Such reduction reactions are typically performed in an ethereal solvent, particularly an ethereal solvent having a b.p. of $\geq 175°$ C., and more particularly an ethereal solvent having a b.p. of $\geq 200°$ C. The tertiary amine may be any of the tertiary amines described above and the tertiary phosphine may be any of the above-described tertiary phosphines. The tertiary amine and/or tertiary phosphine, organic solvent and reducing agent may be combined in any order prior to reaction with the alkylmetal halide. The alkylmetal halide is typically added dropwise, either neat or as a hydrocarbon solution, to an amine-reducing agent and/or phosphine-reducing agent mixture. Typically, the reduction may be performed at a wide range of temperatures. Suitable temperatures for forming the alkylmetal hydride compounds of the present invention are from below ambient temperature to 90° C.

In general, the tertiary amine and/or tertiary phosphine is typically present in a stoichiometric amount based on the number of halogens in the alkylmetal halide, although other suitable amounts may be used. For example, if the alkylmetal halide includes two halogens, then the tertiary amine and/or tertiary phosphine is used at twice the molar amount of the alkylmetal halide. The amount of reducing agent is typically also present in a stoichiometric amount based on the number of halogens in the alkylmetal halide, although other suitable amounts may be used.

Such reduction step may be performed in the same reaction vessel as the transalkylation reaction with the Group IIIA compound, and without isolation or purification of the alkylmetal halide compound. Alternatively, the reduction step may be performed in a continuous manner. For example, a mixture of alkylmetal halide and reducing agent in the desired molar ratio may be added to a tertiary amine and/or tertiary phosphine in a suitable solvent, such as an aromatic or aliphatic hydrocarbon having a b.p. of $\geq 150°$ C. In such a continuous process, the desired alkylmetal hydride may be removed, such as by distillation, while the alkylmetal halide and reducing agent mixture is being added to the reaction vessel. Such continuous operation requires periodic or continuous replenishment of the tertiary amine and/or tertiary phosphine. In a further alternative, the alkylmetal halide and the reducing agent may be independently added in a continuous manner to a reaction vessel containing tertiary amine in a suitable solvent. The addition of the alkylmetal halide and the reducing agent can be controlled by a variety of suitable means, such as by the use of mass flow controllers.

In still another embodiment, alkylmetal compounds including one or more halogens may be reacted with an alkylating agent or an arylating agent or both. Such reaction is typically performed in an organic solvent, and optionally in the presence of a tertiary amine and/or tertiary phosphine. Suitable alkylating agents include, without limitation, alkyllithium compounds and alkylmagnesium halide compounds. Suitable arylating agents include, but are not limited to, aryllithium compounds and arylmagnesium halide compounds. In particular, a tertiary amine and/or tertiary phosphine is used when an aryllithium compound is used. Suitable tertiary amines and tertiary phosphines are those described above.

A wide variety of organolithium compounds may be used. The term "organolithium compounds", as used herein, includes alkyllithium compounds and aryllithium compounds. Such organolithium compounds typically have the formula $R^2Li$ where $R^2$ is $(C_1-C_{10})$alkyl, aryl or $(C_1-C_6)$ alkyl-substituted aryl. The term "$(C_1-C_6)$alkyl-substituted aryl" refers to an aryl group having one or more of its hydrogens replaced with a $(C_1-C_6)$alkyl substituent. Exemplary aryl moieties include phenyl, tolyl, xylyl, naphthyl, biphenyl, benzyl, and the like. As used herein, "aryl" includes $(C_1-C_6)$alkaryls such as benzyl, phenethyl, phenyl propyl and the like. Particularly suitable groups for $R^2$ include, but are not limited to, methyl, ethyl, n-propyl, iso-propyl, n-butyl, iso-butyl, sec-butyl, tert-butyl, cyclopentyl, cyclohexyl, methylcyclohexyl, phenyl, tolyl, and benzyl. Preferred alkyls include, methyl, ethyl, n-propyl, iso-propyl, tert-butyl and iso-butyl. In a particular embodiment, when an aryllithum compound is used a tertiary amine is also used. The organolithium compounds are generally commercially available, such as from Aldrich, or may be prepared by methods known in the art.

A wide variety of organomagnesium halides, i.e. Grignard reagents, may be reacted with the present alkylmetal halides. As used herein, the term "organomagnesium halides" includes alkylmagnesium halides and arylmagnesium halides. Exemplary organomagnesium halides include, without limitation, $(C_1-C_{10})$alkylmagnesium halides, $(C_6-C_{10})$ arylmagnesium halides and $(C_1-C_6)$alkyl-substituted arylmagnesium halides. Such organomagnesium halide compounds are generally commercially available, such as from Aldrich, or may be prepared by known methods. For example, an alkylmagnesium chloride may be prepared by reacting the corresponding alkyl chloride with magnesium metal in ether.

A wide variety of organic solvents may be used in the reaction of the alkylmetal halide with the alkylating agent and/or arylating agent. When an organolithium compound is used, it is preferred that the organic solvent does not contain oxygen. It is further preferred that the organic solvents do not contain dissolved oxygen, i.e. that they are deoxygenated prior to use. The solvents may be deoxygenated by a variety of means, such as purging with an inert gas such as argon or nitrogen, degassing the solvent in vacuo, or a combination thereof. Particularly suitable organic solvents include, but are not limited to, hydrocarbons and aromatic hydrocarbons. Exemplary organic solvents include, without limitation, benzene; alkyl substituted benzenes such as toluene, xylene, and $(C_4-C_{20})$alkyl benzenes such as $(C_{10}-C_{12})$ alkyl benzenes and $(C_{10}-C_{20})$alkyl biphenyls; and aliphatic hydrocarbons such as pentane, hexane, heptane, octane, decane, dodecane, squalane, cyclopentane, cyclohexane, and cycloheptane; and mixtures thereof. More preferably, the organic solvent is benzene, toluene, xylene, $(C_4-C_{20})$ alkyl benzenes, hexane, heptane, cyclopentane or cyclohexane. It will be appreciated that more than one organic solvent may be advantageously used. In an alternative embodiment, the tertiary amine may be used as the organic solvent. When a Grignard reagent is used, the solvent is typically an ethereal solvent or a solvent mixture including an ethereal solvent. Such organic solvents are generally commercially available from a variety of sources, such as Aldrich. Such solvents may be used as is or, preferably, purified prior to use.

In the alkylation or arylation of the present alkylmetal halides, the organolithium compound or organomagnesium compound, organic solvent and optional tertiary amine may be combined in any order prior to reacting with the alkylmetal halide. Typically, the alkylmetal halide is added dropwise, either neat or as a hydrocarbon solution, to the organolithium compound or organomagnesium compound. Suitable temperatures for such reactions are typically from −78° to 80° C. and more typically from −78° C. to ambient. The resulting alkylmetal compounds or alkyl-arylmetal compounds may be used as is or further purified by any suitable techniques, such as those described above. The alkylation or arylation of the alkylmetal halide may be performed in a batch, semi-continuous or continuous manner.

The present alkylmetal compounds are particularly suitable for use as precursors in all vapor deposition methods such as LPE, MBE, CBE, ALD and CVD, and particularly MOCVD and MOVPE. The present compounds are useful for depositing films containing one or more of Group IVA, Group VIA or both Group IVA and Group VIA metals. Such films are useful in the manufacture of electronic devices, such as, but not limited to, integrated circuits, optoelectronic devices and light emitting diodes.

Films of Group IVA and/or Group VIA metals are typically deposited by first placing the desired alkylmetal compound, i.e. source compound or precursor compound, in a delivery device, such as a cylinder, having an outlet connected to a deposition chamber. A wide variety of cylinders may be used, depending upon the particular deposition apparatus used. When the precursor compound is a solid, the cylinders disclosed in U.S. Pat. No. 6,444,038 (Rangarajan et al.) and U.S. Pat. No. 6,607,785 (Timmons et al.), as well as other designs, may be used. For liquid precursor compounds, the cylinders disclosed in U.S. Pat. No. 4,506,815 (Melas et al.) and U.S. Pat. No. 5,755,885 (Mikoshiba et al.) may be used, as well as other liquid precursor cylinders. The source compound is maintained in the cylinder as a liquid or solid. Solid source compounds are typically vaporized or sublimed prior to transportation to the deposition chamber.

The source compound is typically transported to the deposition chamber by passing a carrier gas through the cylinder. Suitable carrier gasses include nitrogen, hydrogen, and mixtures thereof. In general, the carrier gas is introduced below the surface of the source compound, and passes up through the source compound to the headspace above it, entraining or carrying vapor of the source compound in the carrier gas. The entrained or carried vapor then passes into the deposition chamber.

The deposition chamber is typically a heated vessel within which is disposed at least one, and possibly many, substrates. The deposition chamber has an outlet, which is typically connected to a vacuum pump in order to draw by-products out of the chamber and to provide a reduced pressure where that is appropriate. MOCVD can be conducted at atmospheric or reduced pressure. The deposition chamber is maintained at a temperature sufficiently high to induce decomposition of the source compound. The deposition chamber temperature is from 200° to 1200° C., the exact temperature selected being optimized to provide efficient deposition. Optionally, the temperature in the deposition chamber as a whole can be reduced if the substrate is maintained at an elevated temperature, or if other energy such as radio frequency ("RF") energy is generated by an RF source.

Suitable substrates for deposition, in the case of electronic device manufacture, may be silicon, gallium arsenide, indium phosphide, and the like. Such substrates may contain one or more additional layers of materials, such as, but not limited to, dielectric layers and conductive layers such as metals. Such substrates are particularly useful in the manufacture of integrated circuits, opotoelectronic devices and light emitting diodes.

Deposition is continued for as long as desired to produce a film having the desired properties. Typically, the film thickness will be from several hundred angstroms to several tens of nanometers to several hundreds of microns or more when deposition is stopped.

Thus, the present invention provides a method for depositing a film containing one or more of a Group IVA metal, a Group VIA metal or a combination of a Group IVA metal and a Group VIA metal on a substrate including the steps of: a) conveying an alkylmetal source compound in the gaseous phase to a deposition chamber containing the substrate; b) decomposing the alkylmetal source compound in the deposition chamber; and c) depositing a film containing one or more of a Group IVA metal, a Group VIA metal or a combination thereof on the substrate; wherein the alkylmetal compound is prepared by the method including the step of: reacting a metal halide of the formula $R_mMX_{4-m}$ with a Group IIIA compound of the formula $R^1{}_nM^1X^1{}_{3-n}$ in the presence of a tertiary amine and/or tertiary phosphine in an organic solvent to provide an alkylmetal compound, wherein each R is independently chosen from H, alkyl, alkenyl, alkynyl and aryl; M is chosen from a Group IVA metal and a Group VIA metal; each X is independently a halogen; each $R^1$ is independently chosen from $(C_1-C_6)$alkyl; $M^1$ is a Group IIIA metal; each $X^1$ is independently a halogen; m=0–3; and n=1–3.

The present invention further provides a method for manufacturing an electronic device including the step of: depositing a film of a Group VA metal on an electronic device substrate including the steps of: a) conveying an alkylmetal source compound in the gaseous phase to a deposition chamber containing the substrate; b) decomposing the alkylmetal source compound in the deposition chamber; and c) depositing a film containing one or more of a Group IVA metal, a Group VIA metal or a combination thereof on the substrate; wherein the alkylmetal compound is prepared by the method including the step of: reacting a metal halide of the formula $R_mMX_{4-m}$ with a Group IIIA compound of the formula $R^1{}_nM^1X^1{}_{3-n}$ in the presence of a tertiary amine and/or tertiary phosphine in an organic solvent to provide an alkylmetal compound, wherein each R is independently chosen from H, alkyl, alkenyl, alkynyl and aryl; M is chosen from a Group IVA metal and a Group VIA metal; each X is independently a halogen; each $R^1$ is independently chosen from $(C_1-C_6)$alkyl; $M^1$ is a Group IIIA metal; each $X^1$ is independently a halogen; m=0–3; and n=1–3.

The following examples are expected to further illustrate various aspects of the present invention, but are not intended to limit the scope of the invention in any aspect. All manipulations are performed in an inert atmosphere, typically under an atmosphere of dry nitrogen.

EXAMPLE 1

Tetramethylgermane was synthesized according to the following equation.

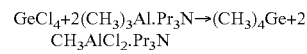

$GeCl_4+2(CH_3)_3Al.Pr_3N \rightarrow (CH_3)_4Ge+2 CH_3AlCl_2.Pr_3N$

To 150 g of high boiling linear alkylbenzenes was added under nitrogen trimethylaluminum (40 g, 0.554 moles) in a 3-necked round-bottomed flask. To this was added n-propylamine (79.5 g, 0.554 moles) dropwise at room temperature. The addition lasted 30 minutes during which the mixture became warm (ca. 50–60° C.). After the addition was complete and the mixture was allowed to cool to room temperature, neat germanium chloride (40 g, 0.186 moles) was added dropwise at room temperature to the adduct formed. The addition took 1 hour during which time the reaction mixture warmed again to ca. 60° C. After cooling to room temperature, the reaction mass was heated to 160–170° C. (oil bath temperature) during which time 20 g of crude Me$_4$Ge distilled through a U-tube into a dry ice cooled receiver. The identity of the product was confirmed by $^1$H nmr (—CH$_3$ resonance at 0.1 ppm) and showed it to contain some tripropyl amine (<5%). Yield of crude product was 81.6%. $^1$H nmr of the remaining pot residues indicated the presence of more tetramethylgermane that was not isolated.

EXAMPLE 2

Tetramethylgermane is expected to be synthesized according to the following equation.

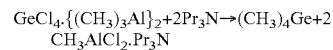

$GeCl_4.\{(CH_3)_3Al\}_2+2Pr_3N \rightarrow (CH_3)_4Ge+2 CH_3AlCl_2.Pr_3N$

To stirred mixture of tripropylamine (144 g, 1.0 mol) in 100 mL high boiling linear alkylbenzenes (Nalkylene alkylate 540 L), is added dropwise a pre-mixed solution of germanium tetrachloride (211 g, 0.99 mol) in trimethylaluminum (72 g, 1.0 mol). The reaction mass is maintained at 85° to 100° C., and the expected crude product is distilled in a continuous manner during the course of addition. The addition and continuous distillation lasts for approximately 3 hours. The expected crude product may then be further purified by fractional distillation and is expected to be tetramethylgermane.

EXAMPLE 3

Diethyl germanium dichloride is expected to be synthesized according to the equation:

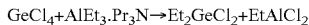
$$GeCl_4 + AlEt_3 \cdot Pr_3N \rightarrow Et_2GeCl_2 + EtAlCl_2$$

To a cool stirred solution of germanium tetrachloride (215 g, 1.0 mole) in hexane (500 mL) maintained at 0° C., is added dropwise a solution of triethylaluminum-tripropylamine adduct prepared with triethylaluminum (114 g, 1.0 mol) and tripropylamine (143 g, 1.0 mol) in 100 mL high boiling linear alkylbenzenes (Nalkylene alkylate 540 L) via pressure equalized addition funnel. The addition lasts for approximately 2 hours. When the addition is complete, the resulting mixture is allowed to slowly warm to room temperature after which a clear solution is expected to be obtained. The hexane solvent is then removed via atmospheric pressure distillation to leave the expected crude product. The reaction mixture is heated to 70° to 80° C. using an oil bath. The expected crude product is further purified via fractional distillation and is expected to yield high purity diethyl germanium dichloride free of metallic impurities and organic solvents.

EXAMPLE 4

Methyltrichlorogermane was synthesized according to the following equation.

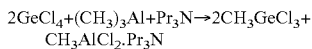
$$2GeCl_4 + (CH_3)_3Al \cdot Pr_3N \rightarrow 2CH_3GeCl_3 + CH_3AlCl_2 \cdot Pr_3N$$

To stirred germanium tetrachloride (209 g, 0.98 mol) maintained at below 40° C. was added dropwise a trimethylaluminum-tripropylamine adduct prepared with trimethylaluminum (35 g, 0.49 mol) and tripropylamine (70 g, 0.49 mol) in 100 mL high boiling linear alkylbenzenes (Nalkylene alkylate 540 L). The addition lasted for 180 minutes. When the addition was completed, the crude product was separated by vacuum distillation. The yield of the crude methyltrichlorogermane (93% purity) was found to be 184 g (97%). The crude product was then further purified by fractional distillation up a 1 foot (30 cm) vacuum jacketed column with stainless steel packing and was confirmed to be the desired product by Fourier transform nuclear magnetic resonance ("FTNMR") (a singlet at 0.98 ppm corresponding to $CH_3$ group).

EXAMPLE 5

Isopropylmethylgermane is expected to be synthesized according to the following equation.

$$CH_3GeCl_3 + (CH_3)_2CHMgCl \rightarrow (CH_3)_2CHGe(CH_3)Cl_2 + MgCl_2$$

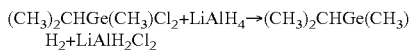
$$(CH_3)_2CHGe(CH_3)Cl_2 + LiAlH_4 \rightarrow (CH_3)_2CHGe(CH_3)H_2 + LiAlH_2Cl_2$$

To a stirred solution of methylgermanium trichloride obtained from Example 4 (52 g, 0.24 mol) in ethyldiglyme (100 mL) maintained at below 40° C. is added dropwise a solution of isopropylmagnesium chloride in butyldiglyme (0.280 mol, 200 mL) via pressure equalized addition funnel. The addition lasts for approximately 180 minutes. When the addition is completed, the reaction mixture is added to a stirred mixture of lithium aluminum hydride (15 g) in ethyldiglyme (200 mL) using a transfer line in a dropwise manner. The expected crude product may be obtained by vacuum distillation and is expected to be isopropylmethylgermane. The expected crude product may be further purified via fractional distillation and is expected to be free of metallic impurities and organic solvents.

EXAMPLE 6

Di-isopropylmethylgermane is expected to be synthesized according to the following equation.

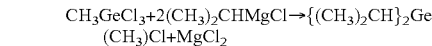
$$CH_3GeCl_3 + 2(CH_3)_2CHMgCl \rightarrow \{(CH_3)_2CH\}_2Ge(CH_3)Cl + MgCl_2$$

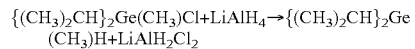
$$\{(CH_3)_2CH\}_2Ge(CH_3)Cl + LiAlH_4 \rightarrow \{(CH_3)_2CH\}_2Ge(CH_3)H + LiAlH_2Cl_2$$

To a stirred solution of methylgermanium trichloride obtained from Example 4 (50 g, 0.23 mol) in ethyldiglyme (100 mL) maintained at below 400° C. is added dropwise a solution of isopropylmagnesium chloride in butyldiglyme (0.560 mol, 400 mL) via pressure equalized addition funnel. The addition lasts for approximately 3 hours. When the addition is completed, the reaction mixture is added to a stirred mixture of lithium aluminum hydride (15 g) in ethyldiglyme (500 mL) using a transfer line in a dropwise manner. The expected crude product may be obtained by vacuum distillation and may be further purified via fractional distillation. The product is expected to be diisopropylmethyl germane and is expected to be free of metallic impurities and organic solvents.

EXAMPLE 7

Diethylisopropylmethylgermane is expected to be synthesized according to the following equation.

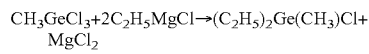
$$CH_3GeCl_3 + 2C_2H_5MgCl \rightarrow (C_2H_5)_2Ge(CH_3)Cl + MgCl_2$$

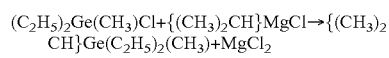
$$(C_2H_5)_2Ge(CH_3)Cl + \{(CH_3)_2CH\}MgCl \rightarrow \{(CH_3)_2CH\}Ge(C_2H_5)_2(CH_3) + MgCl_2$$

To a stirred solution of methylgermanium trichloride obtained from Example 4 (52 g, 0.24 mol) in ethyldiglyme (100 mL) maintained at below 40° C. is added dropwise a solution of ethylmagnesium chloride in butyldiglyme (0.480 mol, 240 mL) via pressure equalized addition funnel. The addition lasts for 180 minutes. When the addition is completed, to the reaction mixture is added a solution of isopropylmagnesium chloride in butyldiglyme (170 mL, 0.24 mol) using a transfer line in a dropwise manner. The addition lasts for approximately 1 hour. The expected crude product may be obtained by vacuum distillation and is expected to be the desired germane. The expected crude product may be further purified via fractional distillation and is expected to be diethylisopropylmethylgermane and is expected to be free of metallic impurities and organic solvents.

EXAMPLE 8

Tetraethylgermane is expected to be synthesized according to the following equation.

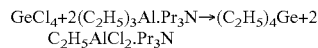
$$GeCl_4 + 2(C_2H_5)_3Al \cdot Pr_3N \rightarrow (C_2H_5)_4Ge + 2C_2H_5AlCl_2 \cdot Pr_3N$$

To stirred germanium tetrachloride (211 g, 0.99 mol) in linear alkylbenzenes (200 mL, Nalkylene alkylate 540 L) maintained at below 40° C. is added dropwise a triethylaluminum-tripropylamine adduct prepared with triethylaluminum (228 g, 2.0 mol) and tripropylamine (285 g, 2.0 mol) in 200 mL high boiling linear alkylbenzenes (Nalkylene alkylate 540 L). The addition lasts for approximately 3 hours. When the addition is completed, the expected crude product is expected to be separated by vacuum distillation. The expected crude product may be further purified by fractional distillation and is expected to be the desired product.

EXAMPLE 9

Dimethyltelluride is expected to be synthesized according to the following equation.

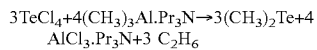
$3TeCl_4 + 4(CH_3)_3Al.Pr_3N \rightarrow 3(CH_3)_2Te + 4 AlCl_3.Pr_3N + 3 C_2H_6$ To stirred suspension of tellurium tetrachloride (269 g, 0.99 mol) in linear alkylbenzenes (200 mL, Nalkylene alkylate 540 L) maintained at below 40° C. is added dropwise a trimethylaluminum-tripropylamine adduct prepared with trimethylaluminum (94 g, 1.3 mol) and tripropylamine (185 g, 1.3 mol) in 200 mL high boiling linear alkylbenzenes (Nalkylene alkylate 540 L). The addition lasts for approximately 3 hours. When the addition is completed, the expected crude product is expected to be separated by vacuum distillation. The expected crude product may be further purified via fractional distillation and is expected to be dimethyltelluride free of metallic impurities and organic solvents.

EXAMPLE 10

The procedure of Example 9 is repeated except that the mole ratio of tellurium tetrachloride to trimethylaluminum-tripropylamine adduct is 1:2, and is expected to yield dimethyltelluride.

EXAMPLE 11

Dimethylselenide is expected to be synthesized according to the following equation.

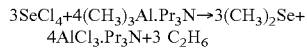
$3SeCl_4 + 4(CH_3)_3Al.Pr_3N \rightarrow 3(CH_3)_2Se + 4AlCl_3.Pr_3N + 3 C_2H_6$ To stirred suspension of selenium tetrachloride (220 g, 0.99 mol) in linear alkylbenzenes (200 mL, Nalkylene alkylate 540 L) maintained at below 40° C. is added dropwise a trimethylaluminum-tripropylamine adduct prepared with trimethylaluminum (95 g, 1.3 mol) and tripropylamine (185 g, 1.3 mol) in 200 mL high boiling linear alkylbenzenes (Nalkylene alkylate 540 L). The addition lasts for approximately 3 hours. When the addition is completed, the expected crude product is expected to be separated by vacuum distillation. The expected crude product may be further purified via fractional distillation and is expected to be dimethylselenide free of metallic impurities and organic solvents.

EXAMPLE 12

Ethyl germanium trichloride is expected to be synthesized according to the equation:

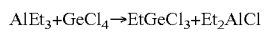
$AlEt_3 + GeCl_4 \rightarrow EtGeCl_3 + Et_2AlCl$

To a cool stirred solution of germanium tetrachloride (50 g, 0.233 moles) in hexane (100 mL) maintained at 0° C., is added dropwise a solution of triethylaluminum-tributylamine adduct (0.233 moles, 70 g) in hexane (50 mL) via pressure equalized addition funnel. This addition lasts for 45 minutes. When the addition is complete, the resulting mixture is allowed to slowly warm to room temperature after which a clear solution is obtained. The hexane solvent is then removed via atmospheric pressure distillation to leave the expected product in crude from. The reaction mixture is heated to 50° to 60° C. using an oil bath. The expected crude product may be further purified via fractional distillation and is expected to yield ethyl germanium trichloride free of metallic impurities and organic solvents.

EXAMPLE 13

The procedure of Example 12 is repeated except that silicon tetrachloride is used instead of germanium tetrachloride and trimethyl aluminum is used instead of triethyl aluminum and is expected to provide methyl silicon trichloride.

EXAMPLE 14

The products in the following table are expected to be prepared according to the following reaction.

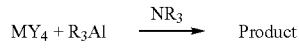
$$MY_4 + R_3Al \xrightarrow{NR_3} Product$$

where $MY_4$, $R_3Al$, $NR_3$ and product are as defined in the table. The abbreviations used have the following meanings: Me=methyl; Et=ethyl; Pr=propyl; i-Bu=iso-butyl; t-Bu=tert-butyl; Bu=butyl; and DMAP=(dimethylamino)propyl.

| $MY_4$ | $R_3Al$ | $NR_3$ | Product |
| --- | --- | --- | --- |
| $GeBr_4$ | $Me_3Al$ | $Et_3N$ | $Me_4Ge$ |
| $MeGeCl_3$ | $Et_3Al$ | $Pr_3N$ | $MeGeEt_3$ |
| $t-BuGeCl_3$ | $Me_3Al$ | $Pr_3N$ | $t-BuGeMe_3$ |
| $Et_2GeCl_2$ | $Me_3Al$ | $Pr_3N$ | $Et_2GeMe_2$ |
| $Me_3GeCl$ | $Pr_3Al$ | $EtNMe_2$ | $Me_3GePr$ |
| $Me_3GeCl$ | $i-Bu_3Al$ | $Pr_3N$ | $i-BuGeMe_3$ |
| $Me_3GeCl$ | $Et_3Al$ | $Et_3N$ | $Me_3GeEt$ |
| $EtGeCl_3$ | $Pr_3Al$ | $Bu_3N$ | $EtGePr_3$ |
| $Et_3GeCl$ | $Me_3Al$ | $Pr_3N$ | $Et_3GeMe$ |
| $t-BuGeCl_3$ | $Et_3Al$ | $Bu_3N$ | $t-BuGeEt_3$ |
| $Me_2GeCl_2$ | $Et_3Al$ | $Pr_3N$ | $Me_2GeEt_2$ |
| $(DMAP)GeCl_3$ | $Me_3Al$ | $Bu_3N$ | $(DMAP)GeMe_3$ |
| $Me_3SiCl$ | $i-Bu_3Al$ | $Pr_3N$ | $i-BuSiMe_3$ |
| $(DMAP)SiCl_3$ | $Me_3Al$ | $Bu_3N$ | $(DMAP)SiMe_3$ |
| $MeSiCl_3$ | $Et_3Al$ | $Pr_3N$ | $MeSiEt_3$ |
| $MeSiCl_3$ | $Pr_3Al$ | $Pr_3N$ | $MeSiPr_3$ |
| $t-BuSiCl_3$ | $Me_3Al$ | $Et_3N$ | $t-BuSiMe_3$ |
| $t-BuSiCl_3$ | $Et_3Al$ | $Bu_3N$ | $t-BuSiEt_3$ |
| $GeCl_4$ | $i-Bu_3Al$ | $Bu_3N$ | $i-BuGeCl_3$ |

EXAMPLE 15

Diethyltelluride is expected to be synthesized according to the following equation.

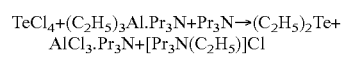
$TeCl_4 + (C_2H_5)_3Al.Pr_3N + Pr_3N \rightarrow (C_2H_5)_2Te + AlCl_3.Pr_3N + [Pr_3N(C_2H_5)]Cl$ To stirred suspension of tellurium tetrachloride (270 g, 1.0 mol) in linear alkylbenzenes (200 mL, Nalkylene alkylate 540 L) maintained at below 40° C. is added dropwise a triethylaluminum-tripropylamine adduct prepared with triethylaluminum (114 g, 1.0 mol) and tripropylamine (285 g, 2.0 mol) in 200 mL high boiling linear alkylbenzenes (Nalkylene alkylate 540 L). The addition lasts for approximately 3 hours. When the addition is completed, the expected crude product is expected to be separated by vacuum distillation. The expected crude product may be further purified via fractional distillation and is expected to be diethyltelluride free of metallic impurities and organic solvents.

What is claimed is:

1. A method of preparing an organometallic compound comprising the step of: reacting a metal halide of the formula $R_mMX_{4-m}$ with a Group IIIA compound of the formula $R^1{}_nM^1X^1{}_{3-n}$ in the presence of a catalyst chosen from a tertiary amine, a tertiary phosphine and mixtures thereof in an organic solvent to provide an alkylmetal compound, wherein each R is independently chosen from H, alkyl, alkenyl, alkynyl and aryl; M is chosen from a Group IVA metal and a Group VIA metal; each X is independently a halogen; each $R^1$ is independently chosen from $(C_1–C_6)$ alkyl; $M^1$ is a Group IIIA metal,; each $X^1$ is independently a halogen; m=0–3; and n=1–3.

2. The method of claim 1 wherein M is chosen from silicon, germanium, tin, tellurium and selenium.

3. The method of claim 1 wherein $M^1$ is chosen from boron, aluminum, gallium, indium and thallium.

4. The method of claim 1 wherein the tertiary amine has the formula $NR^4R^5R^6$, wherein $R^4$, $R^5$ and $R^6$ are independently selected from $(C_1–C_6)$alkyl, di$(C_1–C_6)$alkylamino-substituted $(C_1–C_6)$alkyl and phenyl, and wherein $R^4$ and $R^5$ may be taken together along with the nitrogen to which they are attached to form a 5–7 membered heterocyclic ring.

5. The method of claim 1 wherein the metal halide and the Group IIIA compound are present in a mole ratio of 1:0.1 to 1:5.

6. The method of claim 1 wherein the alkylmetal compound comprises one or more halogens.

7. The method of claim 6 further comprising the step of reacting the alkylmetal compound with a reducing agent to provide an alkylmetal hydride.

8. The method of claim 6 further comprising the step of reacting the alkylmetal compound with an alkylating agent or arylating agent.

9. The method of claim 6 further comprising the step of reacting the alkylmetal compound with a second Group IIIA compound of the formula $R^1{}_nM^1X^1{}_{3-n}$ in the presence of a tertiary amine.

10. The method of claim 1 wherein the reaction is batch, semi-continuous or continuous.

* * * * *